US00PP14091P39

(12) United States Plant Patent
Evers

(10) Patent No.: US PP14,091 P3
(45) Date of Patent: Aug. 26, 2003

(54) HYBRID TEA ROSE PLANT NAMED 'TANALEPIN'

(75) Inventor: Hans-Jürgen Evers, Uetersen (DE)

(73) Assignee: Rosen Tantau Mathias Tantau Nachfolger, Uetersen (DE)

( * ) Notice: Subject to any disclaimer, the term of this patent is extended or adjusted under 35 U.S.C. 154(b) by 36 days.

(21) Appl. No.: 09/963,202

(22) Filed: Sep. 25, 2001

(65) Prior Publication Data

US 2002/0092051 P1 Jul. 11, 2002

(51) Int. Cl.[7] ..... A01H 5/00
(52) U.S. Cl. ..... Plt./137
(58) Field of Search ..... Plt./137

(56) References Cited

U.S. PATENT DOCUMENTS

PP10,999 P * 7/1999 Evers ..... Plt./133

OTHER PUBLICATIONS

UPOV ROM GTITM Computer Database, GTI JOUVE Retrieval Software 2002/02; 2002/05 citation(s) for 'Tanalepin'.*

* cited by examiner

*Primary Examiner*—Bruce R. Campell
*Assistant Examiner*—W C Haas
(74) *Attorney, Agent, or Firm*—Klarquist Sparkman, LLP

(57) ABSTRACT

Hybrid tea rose plant having good flower production of attractive light pink flowers on long stems having long vase life.

1 Drawing Sheet

GENUS AND SPECIES

*Rosa hybrida.*

VARIETY DENOMINATION

TANALEPIN.

SUMMARY OF THE INVENTION

The present invention relates to a new and distinct variety of rose plant of the hybrid tea class which was discovered by me as a spontaneous mutant of the variety TANaledev (U.S. Plant Pat. No 10,999) growing in a greenhouse at Uetersen, Germany.

Asexual reproduction of this new variety by budding, as performed at Uetersen, Germany, shows that its characteristics come true to form and are established and transmitted through succeeding propagations.

COMPARISION WITH PARENT

TANalepin has blossoms of light pink as contrasted with the ivory white blossoms of its parent.

BRIEF DESCRIPTION OF THE ILLUSTRATION

The accompanying illustration shows typical specimens of the vegetative growth and flowers of this new variety depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart, except where ordinary dictionary significance of color is indicated.

Parent: TANaledev.

FLOWER

Observations made in 2001 from plants of 4 years of age grown in a greenhouse environment at Uetersen in Northern Germany.

Blooming habit: Continuous.

Bud:

*Size.*—4 cm long and 4 cm in diameter when the petals start to unfurl.

*Form.*—The bud form is pointed ovoid.

*Color.*—When sepals first divide, bud color is Red Group 55B. When half blown, the upper sides of the petals are Red Group 55B; and the lower sides of the petals are Red Group 55C.

*Sepals.*—Color: Green Group 144A. Length: 3.7 cm. Width: 1.1 cm. Shape: Pointed. Surface texture: Smooth. There are three normally appendaged sepals. There are two unappendaged sepals with smooth edges.

*Receptacle.*—Color: Green Group 143A. Shape: Funnel. Size: Medium, about 4 cm in length. Surface: Smooth.

*Peduncle.*—Length: About 4 cm. Surface: Smooth.

Bloom:

*Size.*—Average open size is 7.8 cm.

*Borne.*—Singly.

*Stems.*—Strength: Strong. Average length is about 70 cm.

*Form.*—When first open: Cup shaped. Permanence: Outer petals curl back.

*Petalage.*—Number of petals under normal conditions: 33.

*Color.*—The upper sides of the petals are Red-Purple Group 59A. The reverse sides of the petals are Red Group 55B. The base of each petal has White Group 49D spot. The major color on the upper side is Red Group 55A.

*Variegations.*—None.

*Discoloration.*—The general tonality at the end of the first day: Fades slightly and continues to fade as blossom ages to Red Group 55D.

*Fragrance.*—None.

Petals:

*Texture.*—Smooth.

*Size.*—Length: 5.3 cm Width: 4.8 cm.

*Shape.*—Heart shaped.

*Margin.*—Smooth.

*Apex shape.*—Pointed.

*Base shape.*—Circular.

*Form.*—Irregular.

*Arrangement.*—Irregular. Petaloids in the center are few and of Red-Purple Group 59A.

*Persistence.*—Petals drop off cleanly before drying.

*Lastingness.*—On the plant: About 16 days. As a cut flower: About 16 days.

Reproductive parts:

*Anthers.*—Length: 0.2 cm Color: Yellow-Orange Group 17A. Arrangement: Randomized.

*Filaments.*—Color: Greyed-White Group 156C. Quantity: 162.

*Pollen.*—Color: Yellow-Orange Group 17A.

*Stamens.*—Number: 63.

*Pistils.*—Number: One. Styles: Color: Yellow-Orange Group 22A. Length: 3 cm. Stigmas: Color: Greyed-White Group 156B. Length: 2 cm.

*Hips.*—None produced.

Plant:

*Form.*—Shrub.

*Growth.*—Upright. At maturity, height is 130 cm, width is 40 cm.

*Rootstock.*—*Rosa canina.*

Foliage: Number of leaflets on normal mid-stem leaves: 5.

*Size.*—Medium (17.4 cm long×11.8 cm wide).

*Quantity.*—Normal.

*Color.*—New and old foliage: Upper side: Yellow-Green Group 147A. Lower side: Yellow-Green Group 147C.

Leaflets:

*Size.*—About 8.7 cm long×4.7 cm wide.

*Shape.*—Broadly oval.

*Tip shape.*—Circular.

*Apex shape.*—Pointed.

*Texture.*—Upper side smooth.

*Edge.*—Serrated.

*Serrations.*—Single.

*Petiole color.*—Yellow-Green Group 146C.

*Petiole rachis.*—Color: Yellow-Green Group 146C. Underside rough.

*Auricle shape.*—Elongated.

*Stipules.*—Length: 3 cm.

*Disease Resistance.*—Susceptible to downy mildew, blackspot and rust.

*Pest persistance.*—Susceptible.

Wood:

*New wood.*—Color: Yellow-Green Group 146A. Bark: Rough.

*Old wood.*—Color: Greyed-Orange Group 165A. Bark: Smooth.

Prickles:

*Quantity.*—On main canes from base: Eighteen on 60 cm stem. On laterals from main canes: Few.

*Form.*—Hooked upward.

*Color when young.*—Greyed-Orange Group 165C.

*Color when mature.*—Greyed-Orange Group 165B.

*Small prickles.*—Quantity: On main stalks: None. On laterals: None.

Winter hardiness: Not winter hardy.

I claim:

1. A new and distinct variety of rose plant of the hybrid tea class, substantially as herein shown and described, characterized particularly by its good production of light pink flowers on long stems having long vase life.

* * * * *

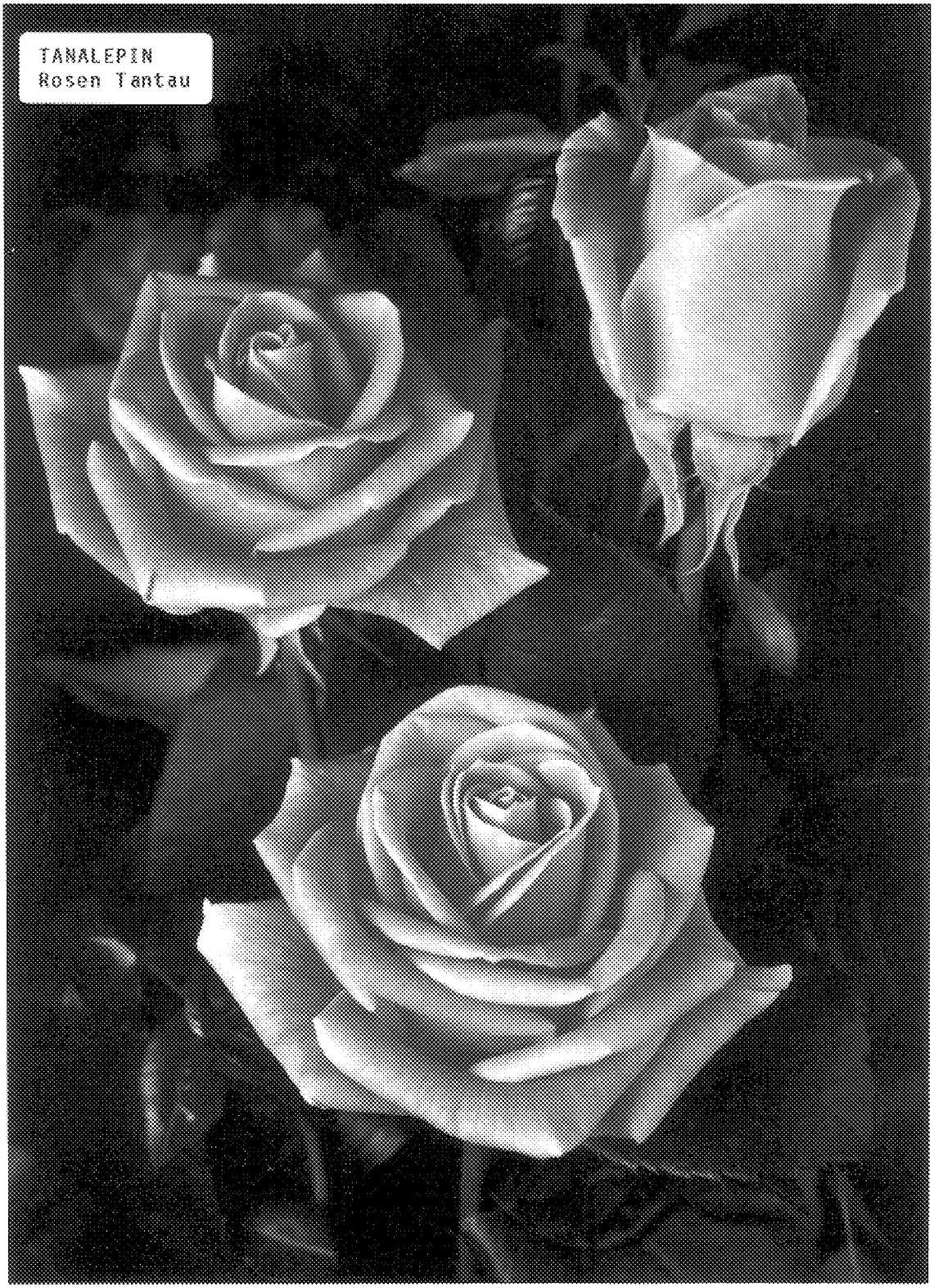
TANALEPIN
Rosen Tantau